US012471957B2

(12) United States Patent
Lavoritano et al.

(10) Patent No.: US 12,471,957 B2
(45) Date of Patent: Nov. 18, 2025

(54) CABLE BONE TRANSPORT DEVICE

(71) Applicant: DePuy Synthes Products, Inc., Raynham, MA (US)

(72) Inventors: Scott Lavoritano, Raynham, MA (US); Benjamin Harnwell, Raynham, MA (US); Joseph Costanzo, Raynham, MA (US); Albert Montello, Raynham, MA (US); Michael Wahl, Raynham, MA (US); Mark Grady, Raynham, MA (US); Vaughn Charlton, III, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 38 days.

(21) Appl. No.: 18/403,386

(22) Filed: Jan. 3, 2024

(65) Prior Publication Data

US 2025/0213276 A1 Jul. 3, 2025

(51) Int. Cl.
*A61B 17/66* (2006.01)
*A61B 17/88* (2006.01)

(52) U.S. Cl.
CPC .......... *A61B 17/66* (2013.01); *A61B 17/8861* (2013.01)

(58) Field of Classification Search
CPC ..... A61B 17/62; A61B 17/66; A61B 17/8861; A61B 17/6433
See application file for complete search history.

(56) References Cited

U.S. PATENT DOCUMENTS 5,429,638 A 7/1995 Muschler et al.
5,431,659 A * 7/1995 Ross, Jr. ............ A61B 17/8869 606/103

(Continued)

FOREIGN PATENT DOCUMENTS

CN 2253961 Y 5/1997
CN 108498149 A 9/2018

(Continued)

OTHER PUBLICATIONS

Baumgart, R , et al., "Bone Transport System with a Central Cable—Fully Automatic, Continuous Distraction Osteogenesis for the Treatment of Large Bone Defects", Biomed. Technik, vol. 49, 2004, 202-207.

(Continued)

*Primary Examiner* — Andrew Yang
(74) *Attorney, Agent, or Firm* — Flaster Greenberg P.C.

(57) ABSTRACT

A bone transport device may include a first support member, a second support member, a plurality of first rods, a cable, and a plurality of actuator assemblies. The cable may be configured to be received through a first bone segment. The bone transport device may further include a second rod that is configured to extend through the first bone segment such that the cable abuts a portion of the second rod within the first bone segment. The plurality of actuator assemblies may be attached to the first support member or the second support member. Each of the plurality of actuator assemblies may include a body, a spool, and an actuator. The actuator may be configured to rotate the spool to wind the cable onto the spool and translate a second bone segment with respect to the first support member and the second support member.

25 Claims, 9 Drawing Sheets

(56) References Cited

U.S. PATENT DOCUMENTS

| | | | | |
|---|---|---|---|---|
| 11,266,454 | B2 * | 3/2022 | Wigginton | A61B 17/8869 |
| 12,137,941 | B2 | 11/2024 | Venturini et al. | |
| 2011/0313418 | A1 * | 12/2011 | Nikonovas | G16H 30/40<br>606/56 |
| 2011/0313419 | A1 | 12/2011 | Mullaney | |
| 2021/0220016 | A1 * | 7/2021 | Bahadir | A61B 17/62 |

FOREIGN PATENT DOCUMENTS

| | | | |
|---|---|---|---|
| CN | 211610018 | U | 10/2020 |
| CN | 220089617 | U | 11/2023 |
| CN | 117137600 | A | 12/2023 |
| DE | 3802743 | A1 | 8/1989 |
| WO | 2024133885 | A1 | 6/2024 |

OTHER PUBLICATIONS

Bernstein, Mitchell , et al., "Tibial Bone Transport Over an Intramedullary Nail Using Cable and Pulleys", Clin Orthop Relat Res., vol. 473, No. 10, Oct. 2015, 3143-53.

Quinnan, Stephen , et al., "Balanced Cable Transport with Circular External Fixation and Then Nailing for Segmental Tibia Bone Defects", 1 page.

* cited by examiner

CABLE BONE TRANSPORT DEVICE

BACKGROUND

External fixation devices are commonly used to fixate, manipulate, distract, or apply force to one or more bone segments for the treatment of various skeletal defects, such as fracture repair, joint fixation, limb lengthening, and deformity correction. External fixation devices may include fixators such as rings and multi-planar or mono-lateral/monorails. Multi-planar external fixators may comprise one or more rings or ring sections attached to pins and/or wires that secure fixation of the bone. A mono-lateral or mono-rail fixator may be attached to pins, wires, or rods. The fixators may interconnect with one or more adjustable struts, to fixate the fracture or the joint, and enabling mono lateral or three dimensional movement of the bone segments.

The length of the struts is typically adjusted manually by the patient, sometimes several times daily in a process might be painful, difficult, and complicated. Lack of compliance, or erroneous adjustment of the struts can cause complications, and is a common contraindication for such procedures.

SUMMARY

The application is generally related to devices and methods used to transport one or more portions of bone toward another portion of bone with an external fixation system.

A bone transport device may include a first support member, a second support member, a plurality of first rods, a cable, and a plurality of actuator assemblies. The first support member and the second support member may be configured to at least partially surround and/or penetrate a body part associated with a bone portion (e.g., a first bone segment). The plurality of first rods may be secured to the first support member and the second support member such that the second support member is spaced a first distance from the first support member in a first direction. The cable may be configured to be received through the first bone segment. The bone transport device may include a second rod configured to extend through the first bone segment such that the cable abuts a portion of the second rod within the first bone segment. The cable may be configured to be secured to a second bone segment. The plurality of actuator assemblies may be attached to the first support member or the second support member. Each of the plurality of first rods may be threaded. Each of the plurality of first rods may be configured to receive a respective first set of nuts on opposed sides of the first support member and a respective second set of nuts on opposed sides of the second support member.

Each of the plurality of actuator assemblies may include a body, a spool, and an actuator. The spool may be supported by the body. The spool may be configured to rotate about a rotational axis to windingly receive the cable. The actuator may be configured to rotate the spool to wind the cable onto the spool and translate the second bone segment with respect to the first support member and the second support member. The second bone segment may be translated toward the first support member as the actuator of each of the plurality of actuator assemblies rotates the respective spool. The actuator may be configured to be removably attached to the body. The second support member may remain the first distance from the first support member as the second bone segment is translated. For example, the second support member may remain the first distance from the first support member as the spool of each of the plurality of actuator assemblies is rotated. The spool may include a barrel and respective flanges on opposed sides of the barrel. The barrel may be tapered from the flanges toward a center of the barrel. The barrel may include a first aperture configured to receive a distal end of the cable. The barrel may include a second aperture that is configured to receive a fastener to secure the distal end of the cable within the first aperture.

The spool may be located proximate to an exit site of the cable. The cable may extend in a second direction from the first bone segment to the spool of one of the plurality of strut assemblies. The second direction may be substantially orthogonal to the first direction. The second rod may include a threaded portion and a non-threaded portion. The cable may be configured to abut the non-threaded portion, for example, to turn the cable from the first direction to the second direction. The second rod may be configured to turn the cable approximately 90 degrees within the first bone segment. The rotational axis of the spool may be substantially parallel to the plurality of first rods. The spool may define a keyway configured to engage an output shaft of the actuator such that the spool is operably coupled to the actuator.

The bone transport device may include a controller that is configured to control the actuator of each of the plurality of actuator assemblies. For example, the controller may be configured to control the actuator of each of the plurality of actuator assemblies to rotate the respective spools simultaneously. The controller may be configured to control the actuator of each of the plurality of actuator assemblies to rotate the respective spools sequentially, for example, in a predetermined sequence. The controller may be configured to control the actuator of each of the plurality of actuator assemblies to rotate the respective spools by the same amount. The controller may be configured to control the actuator of each of the plurality of actuator assemblies to rotate the respective spools at the same speed for the same duration. The controller may be configured to control the actuator of each of the plurality of actuator assemblies to rotate the respective spools at different speeds for different durations. Each of the plurality of actuator assemblies may include a controller that is configured to control the actuator of the respective actuator assembly. Each of the plurality of actuator assemblies may be removably attached to the second support member, for example, to adjust their position on the second support member.

Additional features and advantages are realized through the system of the present invention. Other embodiments and aspects of the disclosure are described in detail herein. For a better understanding of the disclosure with advantages and features, refer to the description and to the drawings.

DETAILED DESCRIPTION

Figure 1:
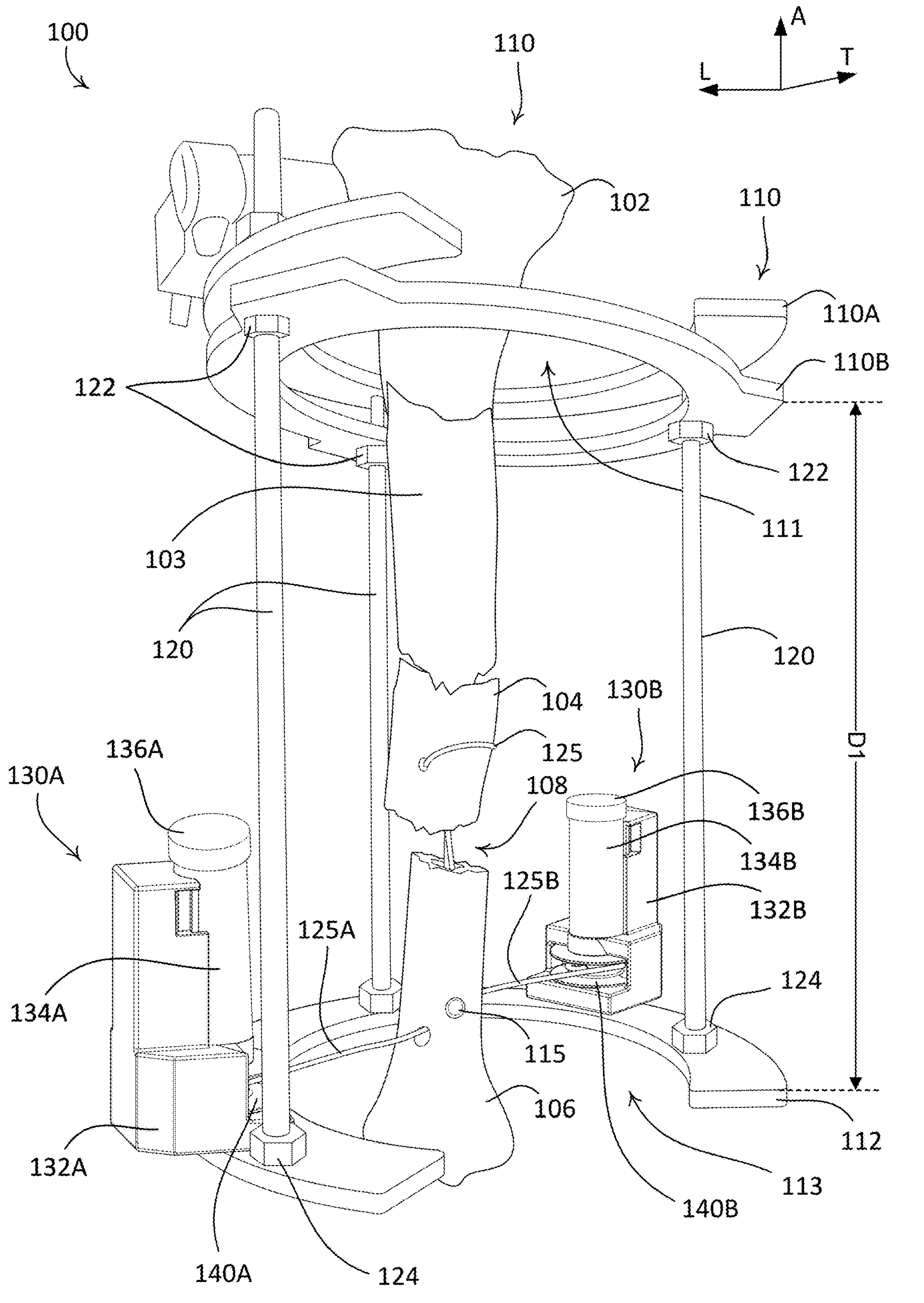
FIG. 1 is a perspective view of an example bone transport device.

In furtherance of the brief description provided above and associated textual detail of each of the figures, the following description provides additional details of example embodiments.

Detailed illustrative examples are disclosed herein. However, specific functional details disclosed herein are merely representative for purposes of describing example embodiments. Examples may, however, be embodied in many alternate forms and should not be construed as limited to only the embodiments set forth herein.

Accordingly, while examples are capable of various modifications and alternative forms, embodiments are shown by way of example in the drawings and will herein be described in detail. It should be understood, however, that there is no intent to limit examples to the particular forms disclosed. To the contrary, examples are to cover all modifications, equivalents, and alternatives falling within the scope of examples.

It will be understood that, although the terms first, second, etc. may be used herein to describe various elements, steps, and/or calculations, these elements, steps, and/or calculations should not be limited by these terms. These terms are only used to distinguish one element, step, and/or calculation from another. For example, a first calculation could be termed a second calculation, and, similarly, a second step could be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises." "comprising," "includes" and/or "including," when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting of example embodiments.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Herein, example embodiments of the present disclosure will be described in detail.

Bone transport is a procedure to facilitate growth of new bone in a region missing a section of bone due to one or more various causes (e.g., such as infection, trauma, disease, etc.). Bone transport may involve an external transport device or an internal transport device. An external bone transport device may be connected to various portions/segments of bone to transport one or more of the various portions/segments of bone toward another portion/segment of bone.

FIG. 1 depicts an example bone transport device 100. The example bone transport device 100 may enable an automated bone transport procedure. The example bone transport device 100 may be used to fix fractures and/or deformations of a tibia. The example bone transport device 100 may prevent the need for a pulley and/or may enable a 2-ring structure design. The bone transport device 100 may generate a better biologic response when compared to other external and internal transport device designs. The bone transport device 100 may enable automation (e.g., automated bone transport).

The example bone transport device 100 may include a first support member 110, a second support member 112, a plurality of first rods 120, a cable 125, and a plurality of actuator assemblies 130A, 130B. The cable 125 may be wound at the exit site (e.g., where the cable exits the patient's body). The first support member 110 may be connected to the second support member 112 using the plurality of first rods 120. Each of the plurality of first rods 120 may be secured to the first support member 110 and the second support member 120 using a plurality of nuts 122.

The plurality of first rods 120 may extend in a first direction. The first direction may be an axial direction A. Each of the plurality of first rods 120 may define threads (e.g., a threaded portion) that are configured to engage corresponding threads of respective nuts of the plurality of nuts 122. Each of the plurality of first rods 120 may be configured to receive a respective first set of nuts 122 on opposed sides of the first support member 110 and a respective second set of nuts 124 on opposed sides of the second support member 112. The first set of nuts 122 may be arranged on both sides of the first support member 110 to secure the first support member 110 at a first location on the plurality of first rods 120. The second set of nuts 124 may be arranged on both sides of the second support member 112 to secure the second support member 112 at a second location on the plurality of first rods 120. For example, each of the plurality of first rods 120 may be secured to the first support member 110 and the second support member 112 such that the first support member 110 is spaced a first distance D1 from the second support member 112. For example, the first location may be spaced from the second location by the first distance D1. The plurality of first rods 120 may be evenly spaced (e.g., circumferentially) about the first support member 110 and the second support member 112.

One or more of the nuts 122 may be adjusted to set the distance D1 between the first support member 110 and the second support member 112 (e.g., between the first location and the second location). For example, when the first set of nuts 122 are adjusted in the appropriate direction(s), the first support member 110 may be translated along the plurality of first rods 120 such that the distance D1 is increased or decreased. When the second set of nuts 122 are adjusted in the appropriate direction(s), the second support member 112 may be translated along the plurality of first rods 120 such that the distance D1 is increased or decreased. An increase in the distance D1 may cause the first support member 110 to move away from the second support member 112.

The first support member 110 and the second support member 112 may be bases, rings, or ring sections that provide support for the bone transport device 100. The first support member 110 may comprise one or more portions (e.g., such as an upper member 110A and a lower member 110B). The upper member 110A may be at least a partial ring (e.g., as shown in FIG. 1). The lower member 110B may be a full ring (e.g., as shown in FIG. 1). It should be appreciated that the first support member 110 (e.g., the upper member 110A and the lower member 110B) and the second support member 112 are not limited to the respective geometries shown in FIG. 1. For example, the first support member 110 may include two or more partial rings or two or more full rings and the second support member 112 may comprise one or more partial rings and/or one or more full rings.

The first support member 110 may define apertures 111, 113 that are configured to receive a bone 101. The bone 101 may be a fractured long bone such as a femur. The bone 101 may include two or more bone portions or segments (e.g., such as a first bone portion 102, a second bone portion 104, and a third bone portion 106 as shown in FIG. 1). The two or more bone portions may be separated by a defect such as a fracture 108. The first bone portion 102 and/or the second bone portion 104 may be referred to as a proximal portion of the bone 101. The third bone portion 106 may be referred to as a distal portion of the bone 101. The first support member 110 and the second support member 112 may be configured to at least partially surround a body part associated with the third bone portion 106. Additionally or alternatively, the first support member 110 and/or the second support member 112 may be configured to penetrate the bone 101 (e.g., one of the first bone portion 102 or the third bone portion 106). For example, the first support member 110 and/or the second support member 112 may include a bone anchor (e.g., such as a Schanz screw). The first support member 110 may define a first aperture 111 that is configured to receive the first bone portion 102. The second support member 112 may define a second aperture 113 that is configured to receive the third bone portion 106. The first aperture 111 may be aligned with the first location and the second aperture 113 may be aligned with the second location. The first support member 110 may be configured to be attached to the first bone portion 102. For example, the first support member 110 may be attached to the first bone portion 102 via Schanz screws.

The second support member 112 may be coupled to the second bone portion 104 via the cable 125. For example, the cable 125 may extend through the third bone portion 106 and into the second bone portion 104. The cable 125 may be secured to the second bone portion 104. For example, the cable 125 may loop through (e.g., and lasso around) the second bone portion 104 such that a middle portion of the cable 125 is secured to the second bone portion 104. A first portion 125A of the cable 125 may extend through the third bone portion 106 to a first actuator assembly 130A. A second portion 125B of the cable 125 may extend through the third bone portion 106 to a second actuator assembly 130B. The first portion 125A may be received (e.g., windingly received) by a first spool 140A of the first actuator assembly 130A. The cable 125 may be 1000 mm cable, 1200 mm cable, or other cable, for example.

It should be appreciated that the cable 125 may be alternatively secured to the second bone portion 104. For example, the bone transport device 100 may include a bone anchor for securing the cable 125 to the second bone portion 104. Additionally or alternatively, the bone transport device 100 may include a double axis climbing cam lock and/or dynacord for securing the cable 125 to the second bone portion 104.

The cable 125 may extend in a second direction from the third bone portion 106 to the spools 140A, 140B of the strut assemblies 130A, 130B. The second direction may be substantially orthogonal to the first rods 120. For example, the second direction may extend in a plane defined by the longitudinal direction L and the transverse direction T. The cable 125 (e.g., the first portion 125A) may be wound about the first spool 140A as the first spool 140A is rotated. The second portion 125B may be received (e.g., windingly received) by a second spool 140B of the second actuator assembly 130B. For example, the cable 125 (e.g., the second portion 125B) may be wound about the second spool 140B as the second spool 140B is rotated.

The bone transport device 100 may be configured such that the cable 125 may be unwound (e.g., to relieve excess tension) from the first spool 140A by rotating the first spool 140A in the opposite direction. The bone transport device 100 may be configured such that the cable 125 may be unwound (e.g., to relieve excess tension in the cable 125) from the second spool 140B by rotating the second spool 140B in the opposite direction.

The actuator assemblies 130A, 130B may be attached to the second support member 112. For example, the actuator assemblies 130A, 130B may be removably attached to the second support member 112 to adjust their position on the second support member 112. For example, the actuator assemblies 130A, 130B may be removed from a position on the second support member 112, relocated at a different position on the second support member 112, and reattached to the second support member 112. It should be appreciated that although the actuator assemblies 130A, 130B are shown in FIG. 1 as being attached to the second support member 112, the actuator assemblies 130A, 130B may be attached to other components of the bone transport device 100 (e.g., such as the first support member 110 and/or one or more of the plurality of first rods 120).

Each of the actuator assemblies 130A, 130B may include a body 132A, 132B, an actuator 134A, 134B, a controller 136A, 136B, and the spool 140A 140B. The body 132A, 132B may be configured to support a respective one of the spools 140A, 140B. The body 132A, 132B may be configured to support a respective one of the actuators 134A, 134B and a respective one of the controllers 136A, 136B. The spools 140A, 140B may be rotated to wind the cable 125 (e.g., the respective first portion 125A and second portion 125B) onto the spools 140A, 140B and translate the second bone portion 104 with respect to the first support member 110 and the second support member 112. As the second bone portion 104 is translated, a fourth bone portion 103 (e.g., new bone growth) may be stimulated (e.g., via biological response) to grow between the first bone portion 102 and the second bone portion 104. For example, the second bone portion 104 may be translated as the fourth bone portion 103 grows toward the third bone portion 106. The fourth bone portion 102 may extend from the first pone portion 102 toward the second bone portion 104. For example, the actuator 134A, 134B may be operably coupled to the respective spool 140A, 140B. The actuator 134A 134B may be configured to rotate the respective spool 140A, 140B to wind the cable 125 onto the spool 140A, 140B. The actuators 134A, 134B may be motors (e.g., such as servo motors). The second bone portion 104 may be translated toward the first support member 110 as the actuator 134A, 134B of each of the actuator assemblies 130A, 130B rotates the respective spool 140A, 140B. The actuators 134A, 134B may be configured to apply between 100N and 1000N tension to the cable 125. The actuators 134A, 134B may configured to enable approximately 20 movements (e.g., bone translations) per day which may enable enhanced biological response.

The controllers 136A, 136B may be configured to control a respective actuator 134A, 134B. The controllers 136A, 136B may receive control signals (e.g., via wired connection or wireless connection) from a main controller (e.g., such as the main controller 500 shown in FIG. 5 and/or the main controller 710 shown in FIG. 7). The controllers 136A, 136B may control the respective actuators 134A, 134B based on the received control signals. Additionally or alternatively, the controllers 136A, 136B may be pre-configured with instructions to control the actuators 134A, 134B.

Figure 4:
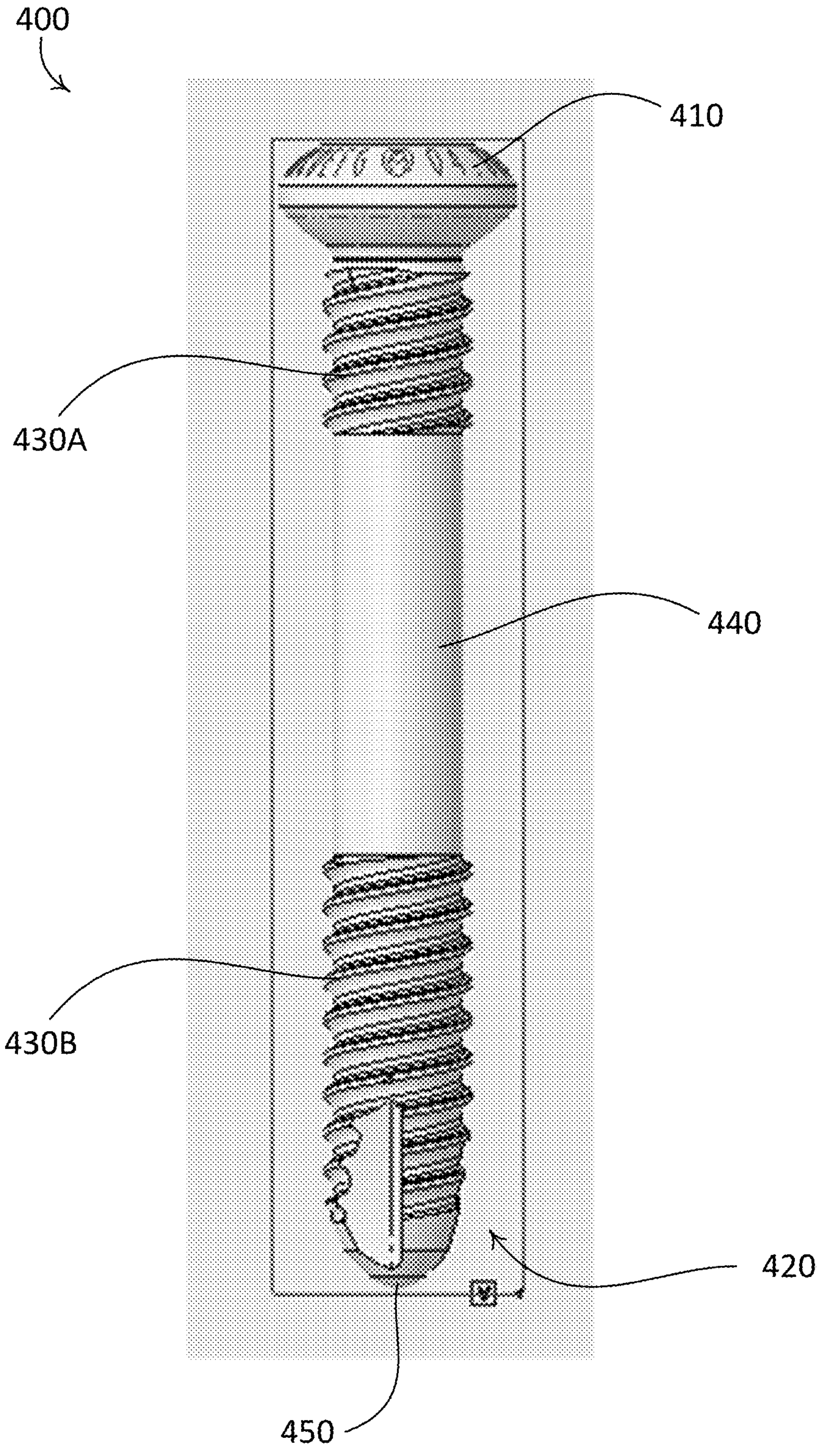
FIG. 4 is a front view of an example rod for use in the bone transport device of FIG. 1.

The bone transport device 100 may include a second rod 115 (e.g., the rod 400 shown in FIG. 4). The second rod 115 may be a screw having a threaded portion and a non-threaded portion. The second rod 115 may be installed within the third bone portion 106. The second rod may be configured to turn the cable 125 approximately 90 degrees within the third bone portion 106. For example, the second rod 115 may define a fulcrum screw for the cable 125. The cable 125 may abut the non-threaded portion as it extends from the third bone portion 106 to the second bone portion 104 such that the cable 125 transitions between the axial direction A and a direction that is parallel to the plane defined by the longitudinal direction L and the transverse direction T. For example, the cable 125 may use the second rod 115 (e.g., the non-threaded portion) as a fulcrum to transfer a force to the second bone portion 104.

The spools 140A, 140B may be located proximate to an exit site (e.g., on the third bone portion 106) of the cable 125. For example, the spools 140A, 140B may be aligned with exit site. The cable 125 may be wound onto the spools 140A, 140B at the exit site. The exit site may be a location where the cable exits the patient's body (e.g., the bone third bone portion 106). For example, the exit site may be in line (e.g., directly in line) with the second rod 115 such that the cable 125 is pulled linearly (e.g., with no dragging or angular forces) from the second rod 115 onto the respective one of the spools 140A, 140B. Winding the cable 125 onto the spools 140A, 140B at the exit site may avoid use of pulleys and may enable use of a two support member (e.g., ring) design. The spools 140A, 140B may define respective rotational axes (e.g., such as rotational axis 221 shown in FIG. 2B) that are substantially parallel to the plurality of first rods 120. It should be appreciated that the spools 140A, 140B may alternatively be arranged such that the rotational axes of the spools 140A, 140B are substantially perpendicular to the plurality of first rods 120. The second support member 112 may remain the first distance D1 from the first support member 110 as the spools 140A, 140B of each of the actuator assemblies 130A, 130B is rotated. For example, the second support member 112 may remain the first distance D1 from the first support member 110 as the second bone portion 104 is translated.

The actuators 134A, 134B may be configured to rotate the spools 140A, 140B in the same direction. The controllers 136A, 136B may include one or more safety features to prevent the actuators 134A, 134B from rotating the spools 140A, 140B in the opposite direction. The one or more safety features may be overridden (e.g., by a physician) to enable temporary rotation of the spools 140A, 140B in the opposite direction.

The bone transport device 100 may include the main controller (e.g., such as the main controller 500 shown in FIG. 5 and/or the main controller 710 shown in FIG. 7) that is configured to control the respective actuators 134A, 134B (e.g., via the controllers 136A, 136B) of each of the actuator assemblies 130A, 130B. The main controller may be configured to control the respective actuators 134A, 134B (e.g., via the controllers 136A, 136B) of each of the actuator assemblies 130A, 130B to rotate the respective spools 140A, 140B simultaneously, by the same amount (e.g., the same angle), and/or at the same speed for the same duration. In examples, the main controller may be configured to control the respective actuators 134A, 134B (e.g., via the controllers 136A, 136B) to rotate the respective spools 140A, 140B sequentially (e.g., in a predetermined sequence). In examples, the main controller may be configured to control the respective actuators 134A, 134B (e.g., via the controllers 136A, 136B) of each of the actuator assemblies 130A, 130B to rotate the respective spools 140A, 140B by different amounts (e.g., to adjust differential tension in the cable 125). In examples, the main controller may be configured to control the respective actuators 134A, 134B (e.g., via the controllers 136A, 136B) to rotate the respective spools 140A, 140B at different speeds and for different durations. For example, the controllers 136A, 136B and/or the main controller may include firmware that enables control of the actuators 134A, 134B. It should be appreciated that although FIG. 1 shows the actuator assemblies 130A, 130B as having controllers 136A, 136B, the controllers 136A, 136B may be omitted from the actuator assemblies 130A, 130B such that the actuators 134A, 134B are controlled by the main controller.

Figure 2A:
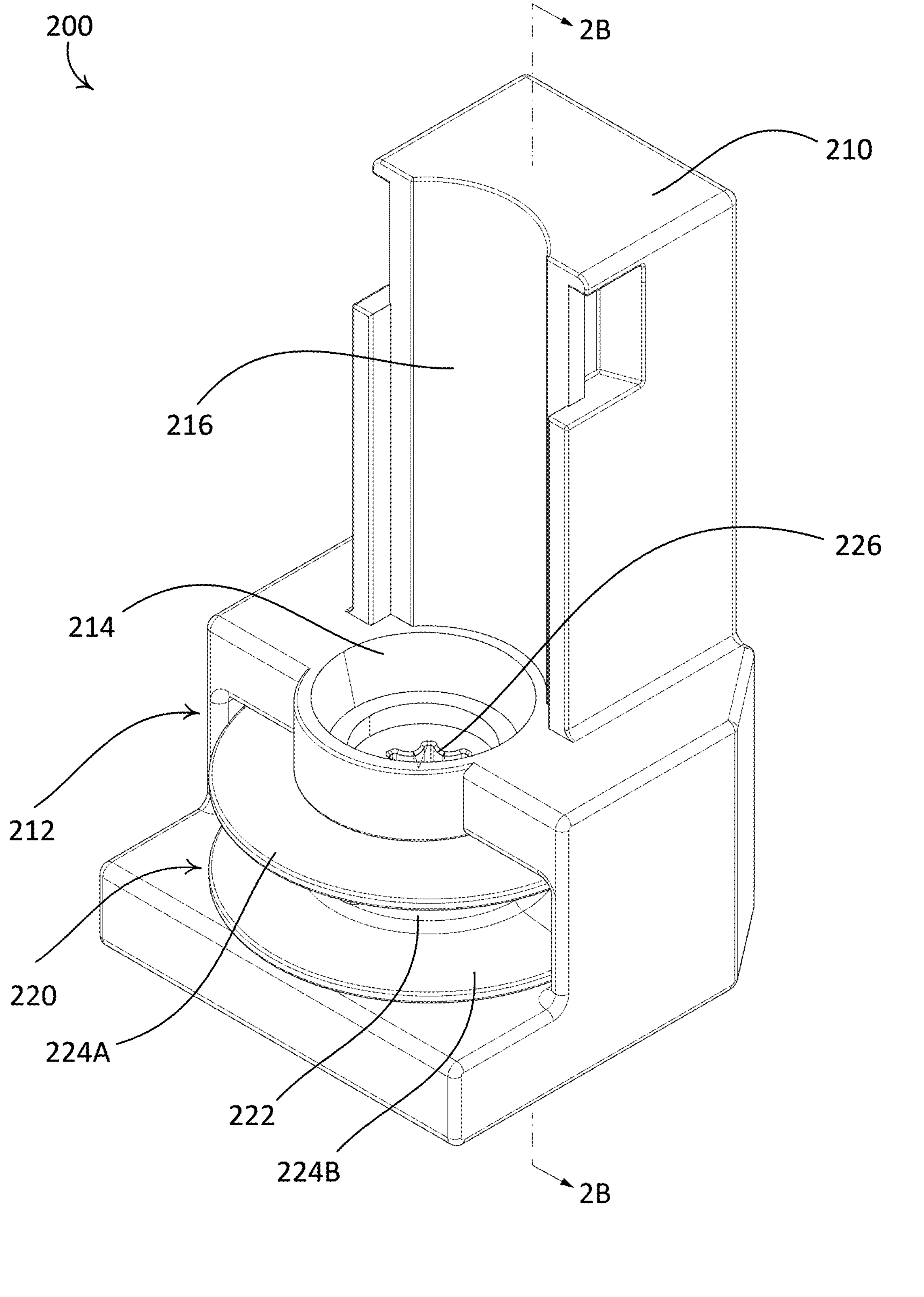
FIG. 2A is a front perspective view of an example actuator assembly in accordance with the bone transport device of FIG. 1.
Figure 2B:
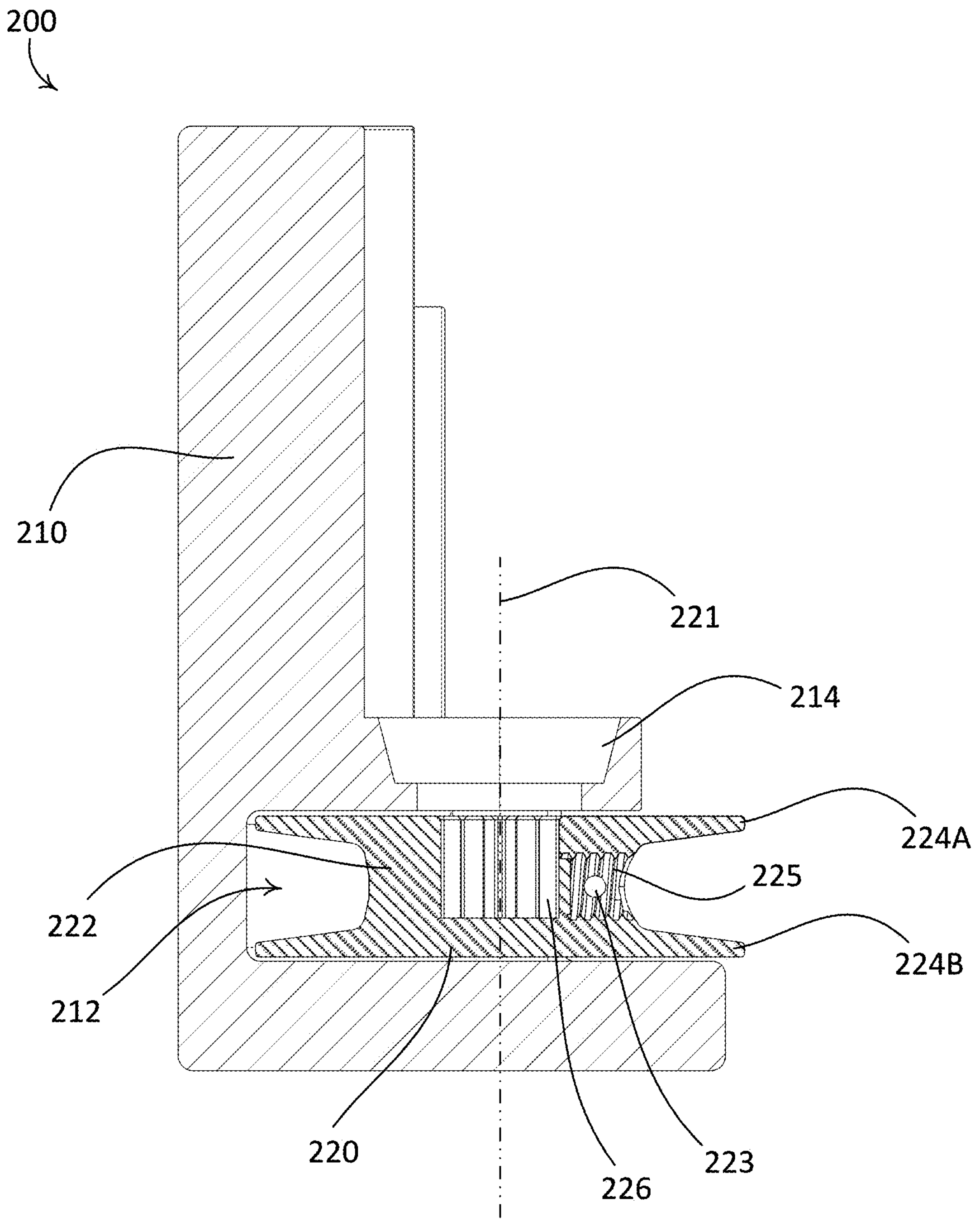
FIG. 2B is a side cross-section view of the example actuator assembly of FIG. 2A.

FIGS. 2A and 2B depict an example actuator assembly 200 (e.g., such as the actuator assemblies 130A, 130B shown in FIG. 1) with an actuator removed. FIG. 2A is a front perspective view of the example actuator assembly 200. FIG. 2B is a side cross-section view of the example actuator assembly 200. The actuator assembly 200 may include a body 210, a spool 220, an actuator (e.g., such as the actuators 134A, 134B shown in FIG. 1), and/or a controller (e.g., such as the controllers 136A, 136B).

The body 210 may define a cavity 212 that is configured to receive the spool 220. The body 210 may further define a hole 214 that is configured to receive an output shaft of the actuator. The body 210 may define a concave upper surface 216 that is configured to be proximate to the actuator. The concave upper surface 216 may define a concavity that corresponds to a convex surface of the actuator.

The spool 220 may include a barrel 222 and respective flanges 224A, 224B on opposed sides of the barrel 222. The barrel 222 may be tapered from the flanges 224A, 224B toward a center (e.g., midpoint) of the barrel 222. The tapered barrel 222 may bias a cable (e.g., such as the cable 125 shown in FIG. 1) toward the center of the barrel 222 as the spool 220 rotates (e.g., as the cable is wound onto the spool 220). The spool 220 may define a rotational axis 221. For example, the spool 220 may be configured to rotate about the rotational axis 221. The rotational axis 221 may extend through a center of the barrel 222.

The barrel 222 may define a first aperture 223 that is configured to receive a distal end of the cable. The first aperture 223 may be a channel that extends through the barrel 222. The barrel 222 may define a second aperture 225 that is configured to receive a fastener (e.g., a set screw) to secure the distal end of the cable within the first aperture 223. For example, the second aperture 225 may be aligned with the first aperture 223 such that the fastener pinches the cable within the first aperture 223. The second aperture 225 may be threaded and configured to engage corresponding threads of the fastener. The first aperture 223 may extend through the second aperture 225 such that the fastener can abut the cable that is extending through the first aperture 223.

The spool 220 may define a keyway 226 that extends into (e.g., through) the barrel 222. The keyway 226 may be configured to engage an output shaft of the actuator such that the spool is operably coupled to the actuator. The keyway

226 may define a keyed pattern cross section that corresponds with the output shaft of the actuator. For example, the keyway 226 and the output shaft of the actuator may define a keyed joint that transfers rotation of the output shaft to the spool 220.

Figure 3A:
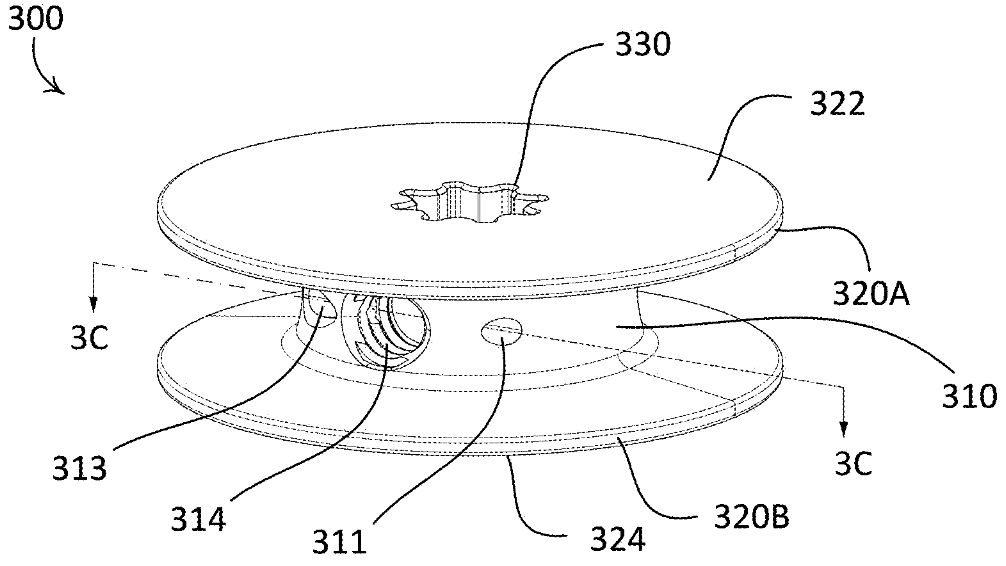
FIG. 3A is a perspective view of an example spool in accordance with the actuator assembly of FIG. 2A.
Figure 3B:
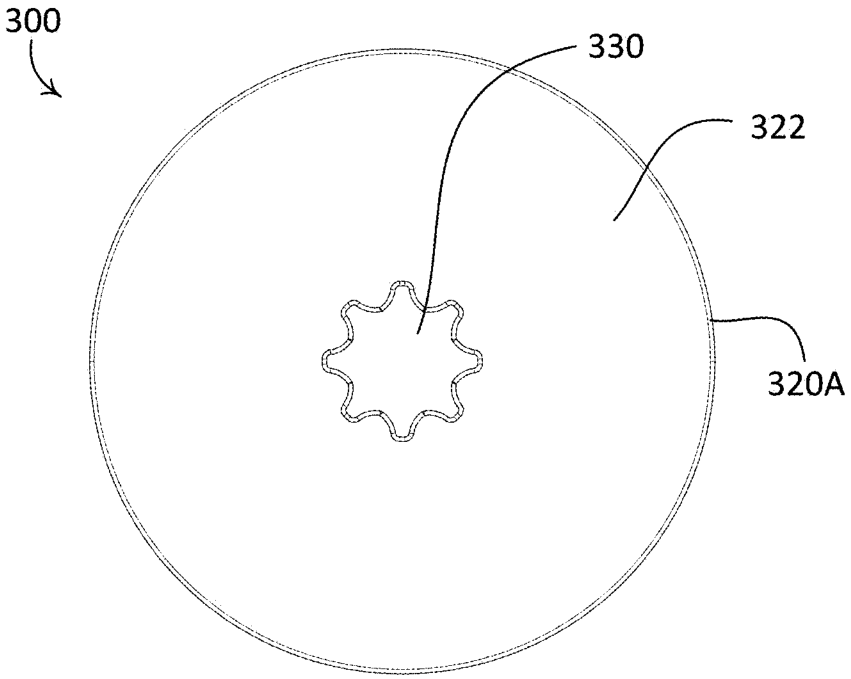
FIG. 3B is a top view of the example spool of FIG. 3A.
Figure 3C:
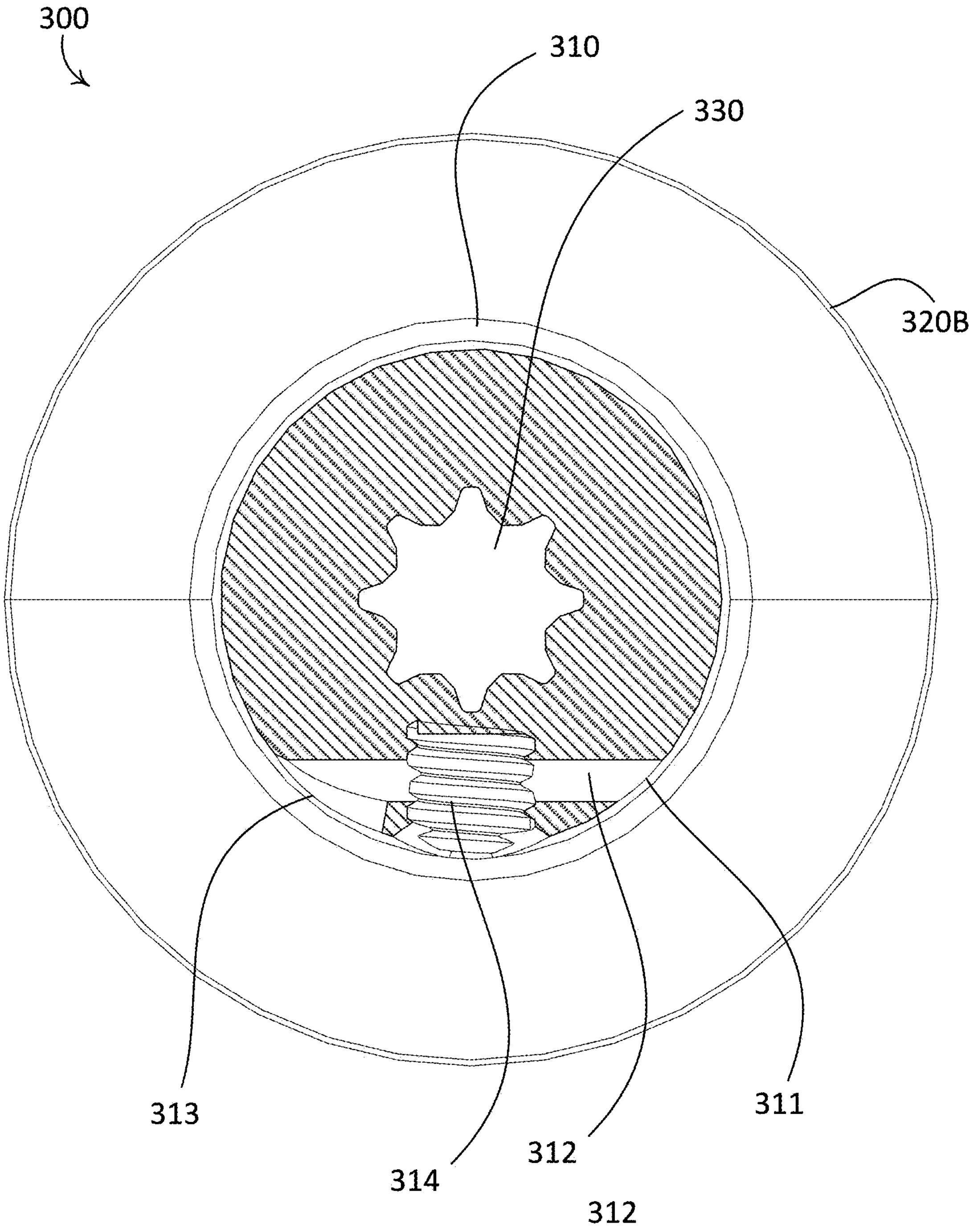
FIG. 3C is a cross-section view of the spool of FIG. 3A.

FIGS. 3A-3C depict an example spool 300 to be used in an actuator assembly (e.g., such as the actuator assemblies 130A, 130B shown in FIG. 1 and/or the actuator assembly 200 shown in FIGS. 2A and 2B) of a bone transport device (e.g., such as the bone transport device 100 shown in FIG. 1). FIG. 3A is a perspective view of the spool 300. FIG. 3B is a top view of the spool 300. FIG. 3C is a cross-section view of the spool 300.

The spool 300 may include a barrel 310, a first flange 320A, and a second flange 320B. The first flange 320A and the second flange 320B may be arranged on opposed sides of the barrel 310. The first flange 320A may define a first outer surface 322 of the spool 300. The second flange 320B may define a second outer surface 324 of the spool 300. The barrel 310 may be tapered from the respective flanges 320A, 320B toward a center (e.g., midpoint) of the barrel 310. The tapered barrel 310 may bias a cable (e.g., such as the cable 125 shown in FIG. 1) toward the center of the barrel 310 as the spool 300 rotates (e.g., as the cable is wound onto the spool 300).

The barrel 310 may define a channel 312 that is configured to receive a distal end of the cable. The channel 312 may be located in an off-center position of the barrel 310. The channel 312 may extend through the barrel 310. The barrel 310 may define a threaded cavity 314 that is configured to receive a fastener to secure the distal end of the cable within the channel 312. The threaded cavity 314 may define internal threads that correspond to the fastener. The channel 312 may extend through the threaded cavity 314 such that the fastener can abut the cable that is extending through the channel 312. The channel 312 may be tapered. For example, the channel 312 may define a first aperture 311 and a second aperture 313. The second aperture 313 may be larger than the first aperture 311.

The spool 300 may define a keyway 330 that extends into (e.g., through) the barrel 310. The keyway 330 may be configured to engage an output shaft of the actuator such that the spool is operably coupled to the actuator. The keyway 330 may define a keyed pattern cross section that corresponds with the output shaft of the actuator. For example, the keyway 330 and the output shaft of the actuator may define a keyed joint that transfers rotation of the output shaft to the spool 300. The keyway 330 may define an octagonal pattern, for example, as shown in FIGS. 3A-3C. It should be appreciated that the keyway 330 is not limited to the geometry shown in FIGS. 3A-3C. Rather, the keyway 330 may define alternate geometry, for example, such as a hexagonal pattern, slotted, a Phillips pattern, a square pattern, a torx pattern, etc.

FIG. 4 is a side view of an example rod 400 (e.g., such as the second rod 115 shown in FIG. 1) to be used with a bone transport device (e.g., such as the bone transport device 100 shown in FIG. 1). The rod 400 may be configured to extend through a bone segment (e.g., such as the third bone portion 106 shown in FIG. 1) such that a cable (e.g., such as the cable 125 shown in FIG. 1) abuts the rod 400 within the bone segment. For example, the rod 400 may be configured to turn the cable approximately 90 degrees (e.g., from a first direction to a second direction that is substantially perpendicular to the first direction) within the bone segment. The rod 400 may be configured to apply a force to the bone segment, for example, in a direction that is substantially perpendicular to the rod 400.

The rod 400 may define a head 410 and a shaft 420. The shaft 420 may define a distal end 450 that is distal from the head 410. For example, the rod 400 may be a screw. The rod 400 may include a threaded portion 430A, 430B and a non-threaded portion 440. For example, the shaft 420 may define the threaded portion 430A, 430B and the non-threaded portion 440. The cable may be configured to abut the non-threaded portion 440 to turn the cable from the first direction to the second direction. The threaded portions 430A, 430B may be on opposed sides of the non-threaded portion 440. For example, the non-threaded portion 440 may be located at a middle portion of the shaft 420. A first threaded portion 430A may be located between the head 410 and the non-threaded portion 440. A second threaded portion 430B may be located between the non-threaded portion 440 and the distal end 450 of the rod 400. For example, the threaded portions 430A, 430B may be configured to engage bone of the bone segment and the non-threaded portion 440 may be configured to be located within an internal cavity of the bone segment.

Figure 5:
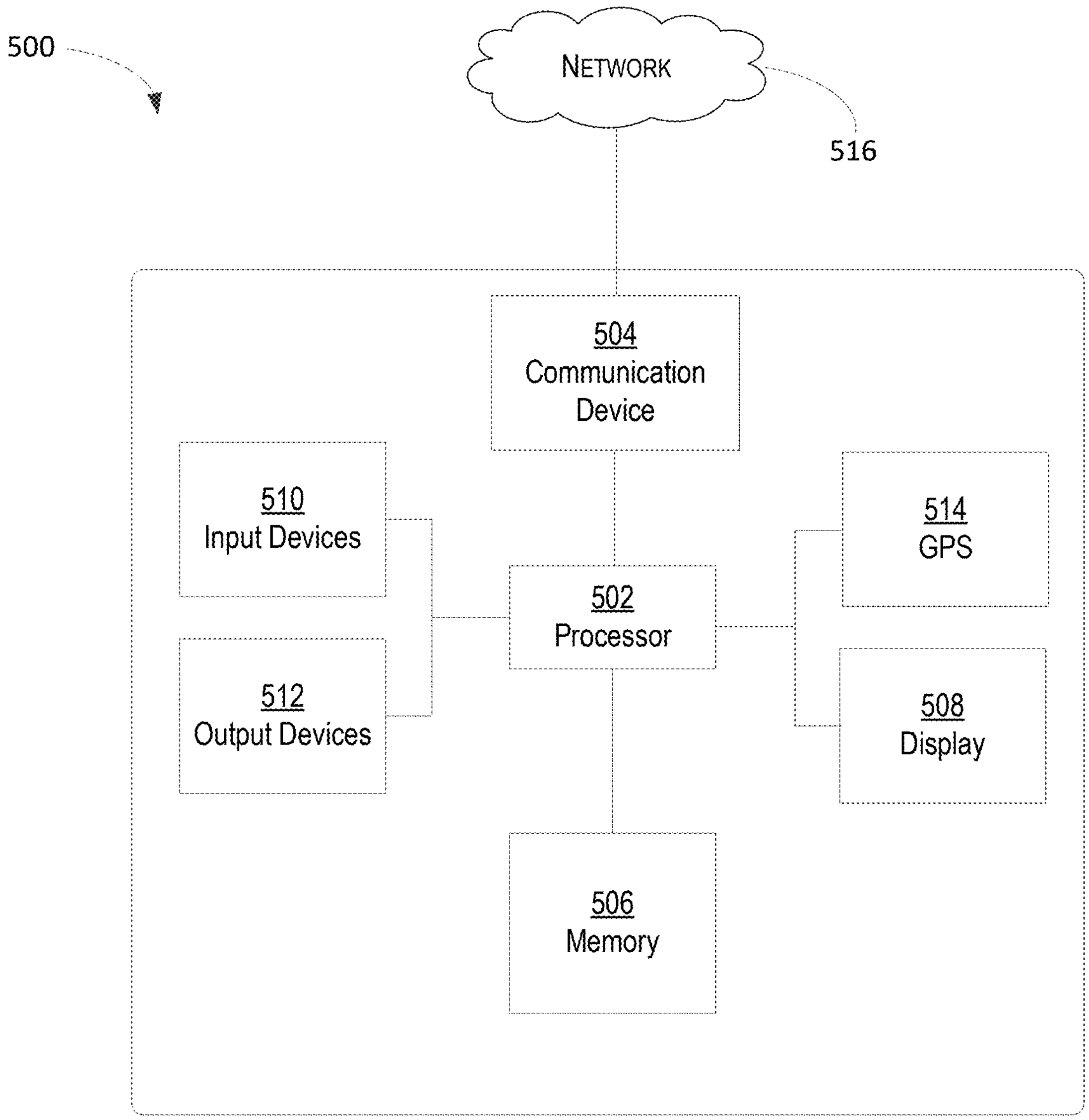
FIG. 5 is a block diagram of an example main controller for use with the bone transport device of FIG. 1.

FIG. 5 depicts a block diagram of an example main controller 500 of a bone transport device (e.g., such as the bone transport device 100 shown in FIG. 1). The main controller 500 may be configured to control a plurality of actuators (e.g., such as the actuators 134A, 134B shown in FIG. 1) and/or a plurality of controllers (e.g., such as the controllers 136A 136B shown in FIG. 1). For example, the main controller 500 may be configured to control the plurality of actuators and/or the plurality of controllers to rotate a spool (e.g., the spools 140A, 140B shown in FIG. 1, the spool 220 shown in FIG. 2, and/or the spool 300 shown in FIGS. 3A-3C) of the bone transport device such that a bone segment is translated as part of a bone transport procedure. The main controller 500 may include a processor 502, a communication interface 504, a memory 506, a display 508, input devices 510, output devices 512, and/or a GPS circuit 514. The main controller 500 may include additional, different, or fewer components.

The processor 502 may include one or more general purpose processors, special purpose processors, conventional processors, digital signal processors (DSPs), microprocessors, integrated circuits, a programmable logic device (PLD), application specific integrated circuits (ASICs), or the like. The processor 502 may perform signal coding, data processing, image processing, power control, input/output processing, and/or any other functionality that enables the main controller 500 to perform as described herein.

The processor 502 may store information in and/or retrieve information from the memory 506. The memory 506 may include a non-removable memory and/or a removable memory. The non-removable memory may include random-access memory (RAM), read-only memory (ROM), a hard disk, or any other type of non-removable memory storage. The removable memory may include a subscriber identity module (SIM) card, a memory stick, a memory card, or any other type of removable memory. The memory 506 may be local memory or remote memory external to the main controller 500. The memory 506 may store instructions which are executable by the processor 502. Different information may be stored in different locations in the memory 506.

The processor 502 that may communicate with other devices via the communication device 504. The communication device 504 may transmit and/or receive information over the network 516, which may include one or more other computing devices or controllers. The communication device 504 may perform wireless and/or wired communications. The communication device 504 may include a receiver, transmitter, transceiver, or other device capable of performing wireless communications via an antenna. The communication device 504 may be capable of communicating via one or more protocols, such as a cellular communication protocol, a Wi-Fi communication protocol, Bluetooth®, a near field communication (NFC) protocol, an internet protocol, another proprietary protocol, or any other radio frequency (RF) or communications protocol. The main controller 500 may include one or more communication devices 504.

The processor 502 may be in communication with a display 508 for providing information to a user. The information may be provided via a user interface on the display 508. The information may be provided as an image generated on the display 508. The display 508 and the processor 502 may be in two-way communication, as the display 506 may include a touch-screen device capable of receiving information from a user and providing such information to the processor 502.

The processor 502 may be in communication with a GPS circuit 514 for receiving geospatial information. The processor 502 may be capable of determining the GPS coordinates of the main controller 500 based on the geospatial information received from the GPS circuit 514. The geospatial information may be communicated to one or more other communication devices to identify the location of the main controller 500.

The processor 502 may be in communication with input devices 510 and/or output devices 512. The input devices 510 may include a camera, a microphone, a keyboard or other buttons or keys, and/or other types of input devices for sending information to the processor 502. The display 508 may be a type of input device, as the display 508 may include touch-screen sensor capable of sending information to the processor 502. The output devices 512 may include speakers, indicator lights, or other output devices capable of receiving signals from the processor 502 and providing output from the main controller 500. The display 508 may be a type of output device, as the display 508 may provide images or other visual display of information received from the processor 502.

Figure 6:
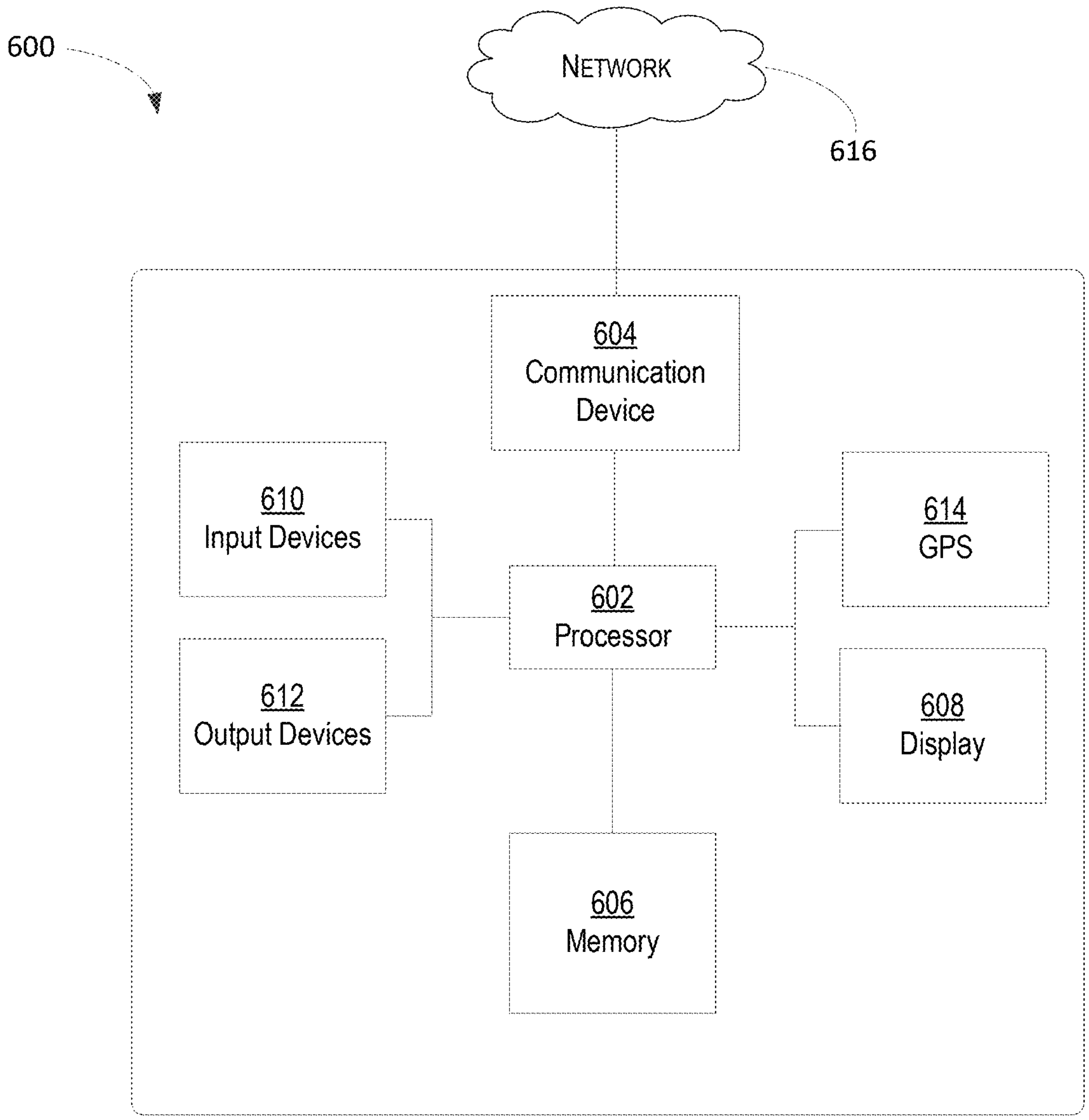
FIG. 6 is a block diagram of an example controller for use with the actuator assembly of FIG. 2A.

FIG. 6 depicts a block diagram of an example controller 600 of an actuator (e.g., such as the actuators 134A, 134B shown in FIG. 1) of an actuator assembly (e.g., such as the actuator assemblies 130A, 130B shown in FIG. 1 and/or the actuator assembly 200 shown in FIGS. 2A and 2B). The controller 600 may include a processor 602, a communication interface 604, a memory 606, a display 608, input devices 610, output devices 612, and/or a GPS circuit 614. The computing device 600 may include additional, different, or fewer components.

The processor 602 may include one or more general purpose processors, special purpose processors, conventional processors, digital signal processors (DSPs), microprocessors, integrated circuits, a programmable logic device (PLD), application specific integrated circuits (ASICs), or the like. The processor 602 may perform signal coding, data processing, image processing, power control, input/output processing, and/or any other functionality that enables the controller 600 to perform as described herein.

The processor 602 may store information in and/or retrieve information from the memory 606. The memory 606 may include a non-removable memory and/or a removable memory. The non-removable memory may include random-access memory (RAM), read-only memory (ROM), a hard disk, or any other type of non-removable memory storage. The removable memory may include a subscriber identity module (SIM) card, a memory stick, a memory card, or any other type of removable memory. The memory 606 may be local memory or remote memory external to the controller 600. The memory 606 may store instructions which are executable by the processor 602. Different information may be stored in different locations in the memory 606.

The processor 602 that may communicate with other devices via the communication device 604. The communication device 604 may transmit and/or receive information over the network 616, which may include one or more other computing devices or controllers. The communication device 604 may perform wireless and/or wired communications. The communication device 604 may include a receiver, transmitter, transceiver, or other device capable of performing wireless communications via an antenna. The communication device 604 may be capable of communicating via one or more protocols, such as a cellular communication protocol, a Wi-Fi communication protocol, Bluetooth®, a near field communication (NFC) protocol, an internet protocol, another proprietary protocol, or any other radio frequency (RF) or communications protocol. The controller 600 may include one or more communication devices 604.

The processor 602 may be in communication with a display 608 for providing information to a user. The information may be provided via a user interface on the display 608. The information may be provided as an image generated on the display 608. The display 608 and the processor 602 may be in two-way communication, as the display 606 may include a touch-screen device capable of receiving information from a user and providing such information to the processor 602.

The processor 602 may be in communication with a GPS circuit 614 for receiving geospatial information. The processor 602 may be capable of determining the GPS coordinates of the controller 600 based on the geospatial information received from the GPS circuit 614. The geospatial information may be communicated to one or more other communication devices to identify the location of the controller 600.

The processor 602 may be in communication with input devices 610 and/or output devices 612. The input devices 610 may include a camera, a microphone, a keyboard or other buttons or keys, and/or other types of input devices for sending information to the processor 602. The display 608 may be a type of input device, as the display 608 may include touch-screen sensor capable of sending information to the processor 602. The output devices 612 may include speakers, indicator lights, or other output devices capable of receiving signals from the processor 602 and providing output from the controller 600. The display 608 may be a type of output device, as the display 608 may provide images or other visual display of information received from the processor 602.

Figure 7:
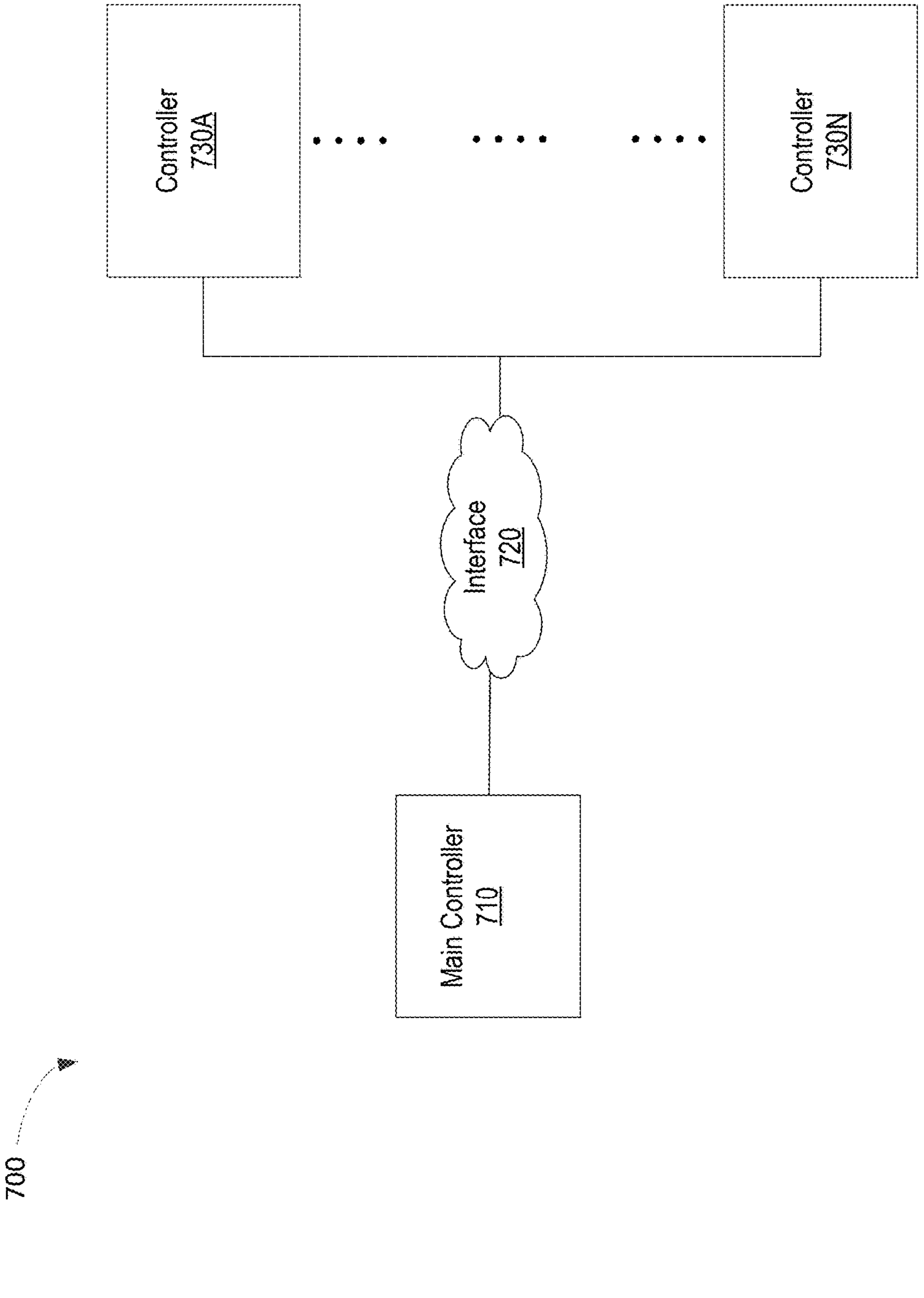
FIG. 7 illustrates a block diagram of the bone transport device of FIG. 1.

FIG. 7 depicts a block diagram of an example bone transport device 700 (e.g., such as the bone transport device 100 shown in FIG. 1), for example, an example control system of the bone transport device 700. The bone transport device 700 may include one or more controllers 730A-730N (e.g., actuator controllers) that may be capable of communicating digital messages with one another, either directly or via the communication interface 720. The one or more controllers 730A-730N may be configured to control a respective actuator (e.g., such as the actuators 134A, 134B shown in FIG. 1). The communication interface 720 may comprise a wired connection and/or a wireless connection between the main controller 710 and the one or more controllers 730A-730N.

The one or more controllers 730A-730N may be capable of communicating messages (e.g., digital messages) to and/or receiving messages (e.g., digital messages) from the main controller 710 via the communication interface 720. The messages received from the main controller 710 may comprise commands for controlling the actuators. Additionally or alternatively, the main controller 710 may be in communication with an application executing locally on the controllers 730A-730N for controlling the actuators.

The main controller 710 may be configured to control the plurality of actuators and/or the one or more controllers 730A-730N of the bone transport device 700 to rotate a spool (e.g., the spools 140A, 140B shown in FIG. 1, the spool 220 shown in FIG. 2, and/or the spool 300 shown in FIGS. 3A-3C) of the bone transport device such that a bone segment is translated as part of a bone transport procedure. The main controller 710 may be operated by an administrative user capable of configuring the bone transport device 700 to control the controllers 730A-730N. The main controller 710 may initiate a configuration session that may be accessed by the controllers 730A-730N via the interface 720.

A bone transport device (e.g., such as the bone transport device 100 shown in FIG. 1) may comprise a floating support member (e.g., ring). The floating support member may be located between an upper support member (e.g., such as the first support member 110 shown in FIG. 1) and a lower support member (e.g., such as the second support member 120 shown in FIG. 1). The cable of the bone transport device may be passed through a bone segment, through the lower support member, and attached to the floating support member. The floating support member may be translated via actuator assemblies to translate the bone segment.

A bone transport device (e.g., such as the bone transport device 100 shown in FIG. 1) may comprise a worm drive schanz pin transport nail that is driven by a worm gear and a schanz screw. The schanz screw may interlock with a gear in the nail and may be driven externally to translate a bone segment.

It should be emphasized that the above-described embodiments of the present disclosure, particularly, any detailed discussion of particular examples are merely possible examples of implementations and are set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A bone transport device comprising:

a first support member;

a second support member;

a plurality of first rods secured to the first support member and the second support member such that the second support member is spaced a first distance from the first support member in a first direction;

a cable configured to be received through a first bone segment and a second bone segment;

a second rod configured to extend through the first bone segment such that the cable abuts a portion of the second rod within the first bone segment; and a plurality of actuator assemblies attached to the first support member or the second support member, wherein each of the plurality of actuator assemblies comprises:

a body;

a spool supported by body, the spool configured to rotate about a rotational axis to windingly receive the cable; and an actuator configured to rotate the spool to wind the cable onto the spool and translate the second bone segment with respect to the first support member and the second support member.

2. The bone transport device of claim 1, wherein the spool comprises a barrel and respective flanges on opposed sides of the barrel, and wherein the barrel is tapered from the flanges toward a center of the barrel.

3. The bone transport device of claim 2, wherein the barrel comprises a first aperture configured to receive a distal end of the cable.

4. The bone transport device of claim 3, wherein the barrel comprises a second aperture that is configured to receive a fastener to secure the distal end of the cable within the first aperture.

5. The bone transport device of claim 1, wherein the spool is located proximate to an exit site of the cable.

6. The bone transport device of claim 1, wherein the cable extends in a second direction from the first bone segment to the spool of one of the plurality of actuator assemblies, and wherein the second direction is substantially orthogonal to the first direction.

7. The bone transport device of claim 6, wherein the second rod comprises a threaded portion and a non-threaded portion, and wherein the cable is configured to abut the non-threaded portion to turn the cable from the first direction to the second direction.

8. The bone transport device of claim 7, wherein the second rod is configured to turn the cable approximately 90 degrees within the first bone segment.

9. The bone transport device of claim 1, wherein the rotational axis of the spool is substantially parallel to the plurality of first rods.

10. The bone transport device of claim 1, further comprising a controller that is configured to control the actuator of each of the plurality of actuator assemblies.

11. The bone transport device of claim 10, wherein the controller is configured to control the actuator of each of the plurality of actuator assemblies to rotate the respective spools simultaneously.

12. The bone transport device of claim 10, wherein the controller is configured to control the actuator of each of the plurality of actuator assemblies to rotate the respective spools sequentially in a predetermined sequence.

13. The bone transport device of claim 11, wherein the controller is configured to control the actuator of each of the plurality of actuator assemblies to rotate the respective spools by the same amount.

14. The bone transport device of claim 11, wherein the controller is configured to control the actuator of each of the plurality of actuator assemblies to rotate the respective spools at the same speed for the same duration.

15. The bone transport device of claim 10, wherein the controller is configured to control the actuator of each of the plurality of actuator assemblies to rotate the respective spools at different speeds for different durations.

16. The bone transport device of claim 1, wherein each of the plurality of actuator assemblies is removably attached to the second support member to adjust their position on the second support member.

17. The bone transport device of claim 1, wherein each of the plurality of first rods are threaded and are configured to receive a respective first set of nuts on opposed sides of the first support member and a respective second set of nuts on opposed sides of the second support member.

18. The bone transport device of claim 1, wherein the second support member remains the first distance from the first support member as the second bone segment is translated.

19. The bone transport device of claim 1, wherein the second support member remains the first distance from the first support member as the spool of each of the plurality of actuator assemblies is rotated.

20. The bone transport device of claim 1, wherein the spool defines a keyway configured to engage an output shaft of the actuator such that the spool is operably coupled to the actuator.

21. The bone transport device of claim 1, wherein the actuator is configured to be removably attached to the body.

22. The bone transport device of claim 1, wherein the second bone segment is translated toward the first support member as the actuator of each of the plurality of actuator assemblies rotates the respective spool.

23. The bone transport device of claim 1, wherein the first support member and the second support member are configured to one or more of at least partially surround or penetrate a body part associated with the first bone segment and the second bone segment.

24. The bone transport device of claim 1, wherein each of the plurality of actuator assemblies further comprises a controller that is configured to control the respective actuator.

25. The bone transport device of claim 1, wherein the cable is secured to the second bone segment.

* * * * *